United States Patent
Saladin et al.

(10) Patent No.: US 7,073,940 B2
(45) Date of Patent: Jul. 11, 2006

(54) APPARATUS FOR MECHANICAL TRANSMISSION

(75) Inventors: Jean-Pierre Saladin, Bagneux (FR); Romain Chatelin, Paris (FR); Celine Pawlak, Plaisir (FR)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 11/053,150

(22) Filed: Feb. 8, 2005

(65) Prior Publication Data
US 2005/0254628 A1 Nov. 17, 2005

(30) Foreign Application Priority Data
May 11, 2004 (FR) .................................. 04 50905

(51) Int. Cl.
*H05G 1/02* (2006.01)

(52) U.S. Cl. ...................................... 378/197; 378/193

(58) Field of Classification Search ................ 378/193, 378/194, 195, 196, 197, 198, 101; 250/370.08, 250/370.09
See application file for complete search history.

(56) References Cited

U.S. PATENT DOCUMENTS

| | | | | |
|---|---|---|---|---|
| 4,987,585 A | * | 1/1991 | Kidd et al. | 378/197 |
| 5,305,363 A | | 4/1994 | Burke et al. | 378/4 |
| 5,486,700 A | | 1/1996 | Silberklang | 250/363.04 |
| 2002/0015469 A1 | | 2/2002 | Oshima et al. | 378/15 |

FOREIGN PATENT DOCUMENTS

WO    WO 00/75691 A1    12/2000

* cited by examiner

*Primary Examiner*—Courtney Thomas
(74) *Attorney, Agent, or Firm*—Cantor Colbunr LLP

(57) ABSTRACT

An X-ray apparatus has hollow motors providing hinge joints for a mobile part in rotation relative to a reference part. Each of the motors includes a rotor fixed to the mobile part as well as a stator fixed to the reference part. The axis of these motors is indistinguishable from the axis around which the mobile part can go into rotation. The motors facilitate an assembling of the parts of the apparatus in permitting cables or wires to cross through the hollow motors. The hinge joints provide a direct transmission between the mobile and reference parts.

52 Claims, 2 Drawing Sheets

APPARATUS FOR MECHANICAL TRANSMISSION

CROSS-REFERENCE TO RELATED APPLICATIONS

This application claims the benefit of a priority under 35 USC 119(a)–(d) to French Patent Application No. 04 50905 filed May 11, 2004, the entire contents of which are hereby incorporated by reference.

BACKGROUND OF THE INVENTION

An embodiment of the present invention is directed to an apparatus for mechanical transmission, and in particular an apparatus having the need for rotatable moving parts relative to each other or in space. An embodiment of the present invention can be applied, but not exclusively, in the field of medical imaging. An embodiment of the present invention can be used, for example, to carry out a radiographic or radioscopic examination or applications. Still further, an embodiment of the invention is directed to an X-ray apparatus and in particular a mobile X-ray apparatus.

There are known mobile X-ray machines comprising mobile parts enabling them to rotate in different directions about a patient. These mobile parts thus enable the orientation of an X-ray beam, so as to analyze a given part of an object to the examined, such as a patient's body. In one example, the orientation of the X-ray beam is useful in that it can be aligned very precisely in one direction of the blood vessel to be analyzed.

There are known apparatus that comprise several driving units to move mobile parts in space. Each of these driving units comprises at least one motor, one belt and one reduction gear. In general, the reduction gear is fastened to a mobile part and is connected to the motor by means of the belt. These driving units limit the total speed of the motor so that the mobile parts of the apparatus move at a limited speed. In a radiographic apparatus, for example, to orient the X-ray beam, high speed is unnecessary and may degrade precision in the movement of the beam.

However, with such driving units, the movements of the mobile parts of the apparatus are not as precise as desired. For example, each part of the X-ray apparatus introduces additional clearance or looseness between itself and the parts to which it is fastened. Since the driving unit comprises at least three parts, there are numerous clearances between these parts. These clearances notably diminish the total precision of the apparatus. These clearances may therefore falsify many movements of the mobile parts of the apparatus.

Furthermore, given the number of parts and the need to minimize the clearances, the assembling of the driving units is often difficult.

In addition, the motors and the reduction gears that comprise the driving unit are solid elements that make it difficult to pass cables and power supply wires into the apparatus. Typically, the cable pass around the reduction gears and motors to connect the elements together. It is therefore difficult to assemble the different elements of the apparatus by means of cables. At certain times, spaces have to be provided along particular parts for the passage of the cables inside the apparatus. The solid nature of the motors therefore constitutes another problem of assembly.

Furthermore, the cables must pass around the motor and/or the reduction gear may raise problems of the premature wearing-out of these cables. In such a configuration, the cables may get folded when the apparatus is in particular positions.

BRIEF DESCRIPTION OF THE INVENTION

An embodiment of the invention comprises hollow motors by which the parts of the apparatus are hinged with one another. The hollow motors each comprise a ring-shaped rotor that is fastened to a mobile part of the apparatus as well as a ring-shaped stator that is fastened to a fixed part of the apparatus. In general, the stator is positioned so as to surround the rotor. The hollow motors therefore limit the clearances in the apparatus because only the clearance existing inside the motor can have an effect on the general precision of the apparatus. This clearance is furthermore very low, in the range of one millimeter.

Furthermore, since the rotor and the stator are ring-shaped, they permit cables to pass inside the motor. It is therefore easier to make an assembly of cable-connected parts since it is no longer necessary to circumvent solid parts of the driving assemblies and the position of the hinges and joints.

Furthermore, the cables pass through the center of the motor and are therefore less likely to fold during rotations of the motor. The hollow motors therefore limit wear and tear in the cables.

An embodiment of the present invention relates to a radiography apparatus comprising: means for providing a source of radiation, such as an X-ray tube that emits an X-ray beam along a direction of emission; means for detecting the emitted radiation after passing through an object to be examined, such as an X-ray detector located so as to be opposite the emitter and in the direction of emission; at least one mobile element, the at least one mobile element being capable of going into rotation about a rotation axis relative to a reference element, the at least one mobile element providing for a movement of the means for providing a source of radiation and of the means for detection in space; at least one hollow motor comprising a ring-shaped stator and a ring-shaped rotor, the hollow portion of the motor being oriented in the axis of the motor and being located about the motor axis, the motor axis being indistinguishable from the rotational axis about which the mobile elements may go into rotation.

BRIEF DESCRIPTION OF THE DRAWINGS

An embodiment of the present invention will be understood more clearly from the following descriptions and from the figures that accompany it. These figures are given purely by way of an example and in no way restrict the scope of the invention. Of these figures.

DETAILED DESCRIPTION OF THE INVENTION

Figure 1A:
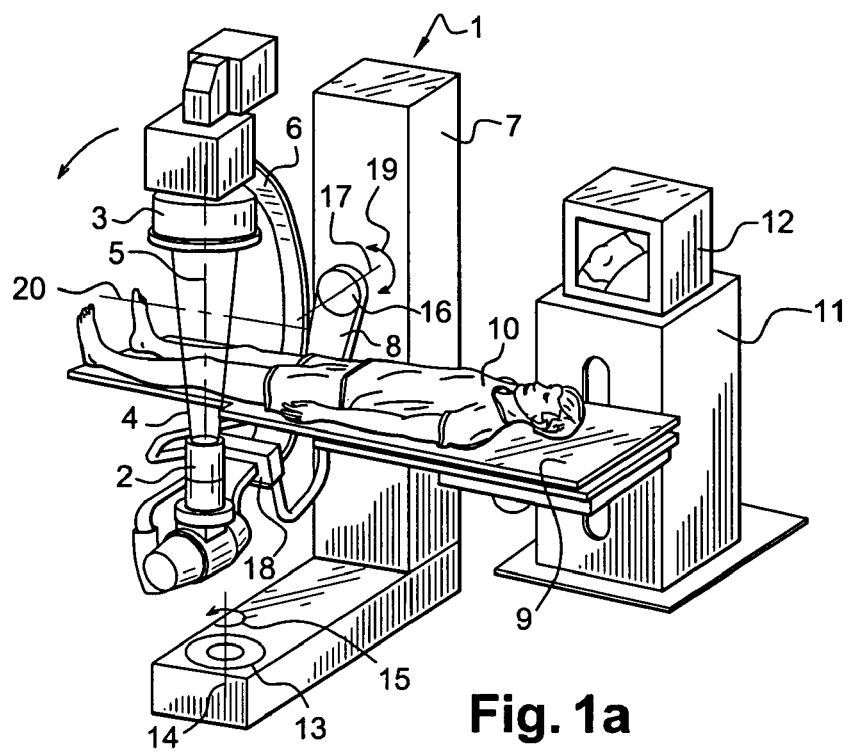
FIG. 1a is a perspective schematic view of a vascular type of X-ray apparatus.

FIG. 1a is a view in space of an X-ray apparatus. More specifically, the apparatus 1 is known as a vascular type of apparatus comprising means for providing a source of radiation, typically an X-ray tube 2 as well means for detecting the radiation, such as an X-ray detector 3. Tube 2 emits an X-ray beam 4 along a directions 5 of emission. Tube 2 and the detector 3 are both hooked or fastened to end, on either side, of a C-shaped arm 6. The detector 3 is fastened to the arm 6 opposite the tube 2 and in the direction 5 of emission so as to receive the X-ray beam. Furthermore, the arm 6 is connected to an L-shaped post 7 by means of an intermediate arm 8. A collimator located inside the detector 3 can imprint a shape on the X-ray beam 4 emitted by the tube 2. Thus, this collimator could modify the width of the beam 4.

A bed or table 9, on which a patient 10 reclines, is fixed and fastened to a frame 11. Bed 9 is placed within the C-shaped arm 6 so that the tube 2 is beneath bed 9 and the detector 3 is above bed 9. Whatever the examination made, the tube 2 and the detector 3 always keep this spatial configuration. Thus, after having received beam 4 that crosses a part of the patient's body, detector 3 emits electrical signals corresponding to the intensity of the rays received. These electrical signals may then be transmitted to a computer 12 by means of wire links that are not shown. The electrical signals enable computer 12 to produce an image corresponding to the analyzed part of the body. The image may be viewed, for example, by means of a screen on the computer 12 in a radioscopy examination or printed in a radiography examination or stored in an appropriate media.

In order to enable a study of each part of the body of the patient 10, the beam 4 can be oriented in a multitude of directions around the patient. Generally, a user or practitioner can modify the position of tube 2 and the detector 3. The L-shaped post 7, the intermediate arm 8 and the C-shaped arm 6 are all three axis hinged relative to one another. The L-shaped post 7 is hinged on the ground (which can be likened to the fixed frame 11) by means of a first hollow motor 13. Motor 13 thus enables the post 7 to rotate on a vertical axis 14. In an embodiment, post 7 may rotate about the patient 10 at an angle 15 ranging from 320° to 350°.

Furthermore, intermediate arm 8 is hinged on the post 7 by means of a second hollow motor 16. Second motor 16 thus enables the intermediate arm 8 to rotate about a horizontal axis 17 that is perpendicular to a face of the post 7. In an embodiment, intermediate arm 8 may rotate about axis 17 at an angle 19 ranging from 320° to 350°.

The C-shaped arm 6 can slide around a link 18. Thus, arm 6 may rotate about an axis 20 that passes through the center of a disk described by two C-shaped arms placed side by side. Axis 20 is furthermore perpendicular to the axis 17 and to the axis 14 for the position shown.

In combining the rotational motions about the three axes 14, 17 and 20, the beam 4 of rays can describe all the directions of emission of the X rays contained within a sphere. Through the motor 13 and 16 and the link 18, the beam 4 can thus cross each part of the patient in a multitude of possible orientations.

The vascular type apparatus 1 as described has a C-shaped arm 6. However, as a variant, arm 6 may have other shapes, such as for example a U shape.

Figure 1B:
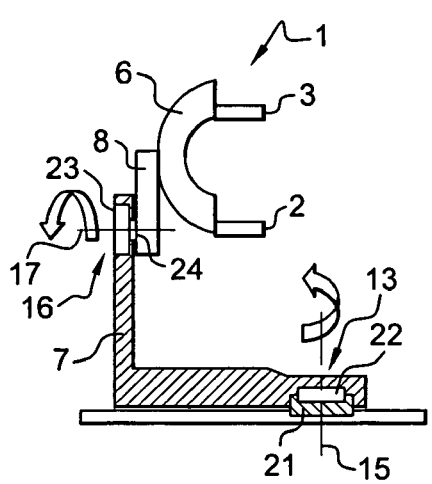
FIG. 1b is a schematic side view of a vascular apparatus.

FIG. 1*b* shows a side view of an apparatus 1 without bed 9 for patient 10. FIGS. 1*a* and 1*b* show hollow motors 13 and 16 respectively providing for the hinging of L-shaped post 7 and of intermediate arm 8. More specifically, FIGS. 1*a* and 1*b* show that the motor 13 has a ring-shaped stator 21 fastened to the ground that is fixed. Motor 13 also has a ring-shaped rotor 22 that is hooked to post 7 that is mobile. Motor 13 thus enables the rotation of post 7 relative to the ground, about the axis 14. One axis of motor 13 corresponds to the axis of stator 21 and of rotor 22 and is furthermore indistinguishable from axis 14.

FIG. 1*b* also shows that motor 16 has a ring-shaped stator 23 fastened to post 7, relative to which intermediate arm 8 is mobile. Motor 16 has a ring-shaped rotor 24 that is fastened to intermediate arm 8. Rotor 16 thus enables the rotation of C-shaped arm 6 relative to post 7 about axis 17. One axis of motor 16, corresponding to the axis of stator 23 and of rotor 24, is furthermore indistinguishable from axis 17.

Thus, in general, in order to hinge parts of the apparatus according to an embodiment of the invention, a rotor is attached a first part that is rotationally mobile relative to a second part while a stator is fastened to this second part.

As a variant, it is possible to use more than two hollow motors such as the motor 13 or motor 16, so as to further increase the number of degrees of freedom of the apparatus 1. Increasing the degrees of freedom of this system facilitates the movement of tube 2 and detector 3. It is thus possible to achieve a precise given position in several different ways.

Figure 1C:
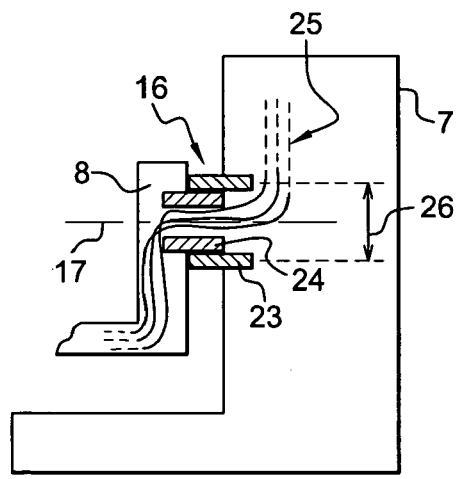
FIG. 1c is a diagrammatic view of a hinge joint of an apparatus made out of a hollow motor.

FIG. 1*c* shows a cross-section view of hollow motor 16 as seen from the side. Hollow motor 16 provides for the rotation of intermediate arm 8 relative to L-shaped post 7 about axis 17. FIG. 1*c* shows that stator 23 and rotor 24, respectively, fastened to arm 8 and post 7, are both ring-shaped and therefore hollow. The hollow generated by the shape of the stator 23 and of the rotor 24 is oriented in axis 17 and is located about axis 17. Stator 23 of motor 16 herein surrounds rotor 24, but it is quite possible to envisage an embodiment of a motor 16 in which rotor 24 surrounds stator 23. The functional operation of motors 13 and 16 can be likened to that of a motorized ball bearing.

In an embodiment, ring-shaped stator 23 has a diameter 26 ranging from 300 to 500 mm. Diameter 26 corresponds to the diameter of motor 16. Diameter of rotor 24 for its part is smaller than the diameter of stator 23 since it is contained by stator 23. The greater the diameter of stator 23 and of rotor 24, the greater, naturally, is the increase in the torque developed by hollow motor 16.

Furthermore, the ring shape of motor 16 can enable cables or wires 25 to cross it. This crossing of cables or wires facilitates an assembling of elements of the apparatus. It is not necessary to provide for particular passages about motor 16 to obtain the passage of cables or wires 25 that connect elements (not shown) to one another.

Furthermore, since the cables or wires are allowed to pass on the whole through the center of the motors, their torque during a rotation of the arm 8 is highly limited. Consequently, the cables or wires 25 are less subject to breakage and their longevity is increased.

In an embodiment, motor 16 can be a direct-current contactless or brushless motor. Thus, there is no contact between rotor 24 and stator 23. The absence of contact makes it possible especially to increase the life of motor 16.

There is no intermediate element between motor 16 and a driving element of arm 8. Motor 16 itself acts as the driving element of arm 8. The gear reduction ratio of such a motor is therefore equal to 1. Arm 8 can thus be very precisely controlled with parts that comprise a minimum clearance between them.

In general, to stop the rotation of motors 13 or 16, a failsafe brake is used. Since a feedback control of the position of the motor is furthermore achieved, it is possible to stop motors 13 or 16 very precisely in a position desired by a user. As a variant, the brake used is a brake comprising a disk.

The description of motor 13 is similar to the description of motor 16 given here in detail. A difference lies in the parts hinged on the motors 13 and 16. As disclosed the hinged parts are orthogonal to each other as is the motors 13 and 16 and as is the axes 14, 17 and 20.

Figure 2A:
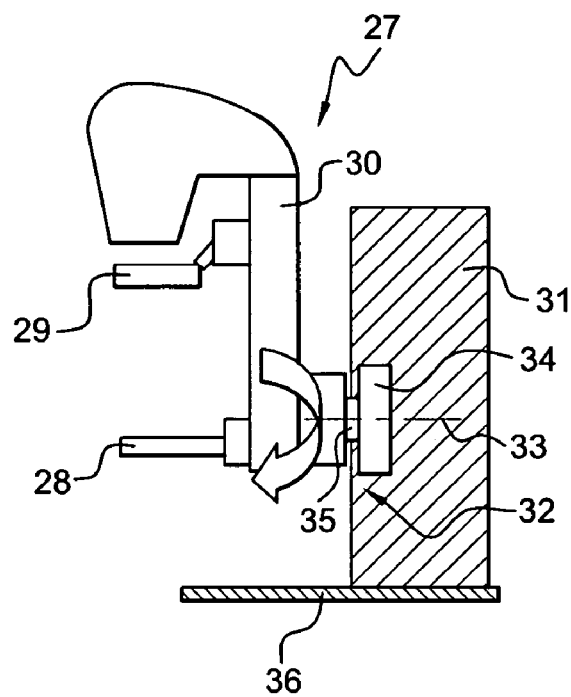
FIG. 2 shows diagrammatic views of a mammography apparatus.
Figure 2B:
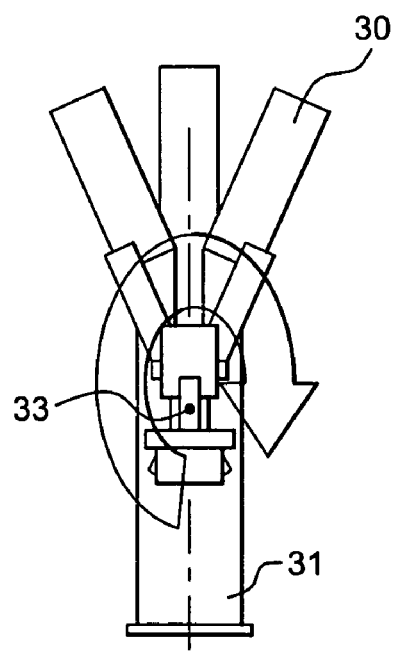

FIGS. 2a and 2b show an embodiment of a mammography apparatus 27. Mammography apparatus 27 comprises means for providing a source of radiation, such as an X-ray tube 28 and means for detecting the radiation, such as an X-ray detector 29. Tube 28 and detector 29 are both attached to a support 30 that is itself linked to a fixed pedestal 31 by means of a hollow motor 32. Motor 32 enable arm 30 to pivot relative to pedestal 31, about an axis 33 parallel to ground 36.

The hinging points of mammography apparatus 27 are made very similarly to those of the vascular type apparatus 1. A stator 34 of motor 32 is fastened to a fixed part herein corresponding to pedestal 31, while a ring-shaped rotor 35 of motor 32 is fastened to a mobile part herein corresponding to arm 30.

FIG. 2b shows a side view of the mammography apparatus 27. FIG. 2b shows that motor 32 permits support 30 to rotate about axis 33, which herein is perpendicular to the plane of the figure. A brake can also be provided for the motor 32.

Whether it is for the vascular type apparatus 1 or the mammography apparatus 27, an embodiment of the invention limits the number of parts used since only one motor provides a hinging between two elements. The precision of these apparatus is therefore increased while the risks of poor assembly are reduced. Furthermore, since the direct-current motor causes very little friction, there is a reduction in friction between parts. The control of the movements and their repeatability are therefore optimized. Since the hollow motors are directly placed on the link to be hinged, it is no longer necessary to use the above-mentioned driving units. An embodiment of the present invention therefore resolves the problem of premature wear and tear, problems of precision as well as those of assembly. An embodiment of the invention therefore increases the precision of such an apparatus while at the same time facilitating assembly of its elements.

One skilled in the art may make or propose various modifications to the structure/way and/or function and/or results and/or steps of the disclosed embodiments and equivalents thereof without departing from the scope and extant of the invention.

What is claimed is:

1. A radiography apparatus comprising:
   means for providing a source of radiation that emits a beam along a direction of emission;
   means for detecting the radiation located so as to be opposite the emitter and in the direction of emission;
   at least one mobile element being capable of going into rotation about a rotation axis relative to a reference element;
   the at least one mobile element providing for a movement of the means for providing a source of radiation and the means for detecting in space;
   at least one hollow motor comprising a ring-shaped stator and a ring-shaped rotor; and
   the hollow portion of the motor being oriented on an axis of the motor and being located about the motor axis, the motor axis being indistinguishable from the rotational axis about which the mobile elements may go into rotation.

2. The apparatus according to claim 1 wherein the ring-shaped rotor is fixed to the mobile element while the ring-shaped stator is fixed to the reference element.

3. The apparatus according to claim 1 wherein the ring-shaped stator surrounds the ring-shaped rotor.

4. The apparatus according to claim 2 wherein the ring-shaped stator surrounds the ring-shaped rotor.

5. The apparatus according to claim 1 wherein the ring-shaped stator has a diameter ranging from 300 to 500 mm.

6. The apparatus according to claim 2 wherein the ring-shaped stator has a diameter ranging from 300 to 500 mm.

7. The apparatus according to claim 3 wherein the ring-shaped stator has a diameter ranging from 300 to 500 mm.

8. The apparatus according to claim 1 wherein the hollow motor is a direct-current contactless or brushless motor.

9. The apparatus according to claim 2 wherein the hollow motor is a direct-current contactless or brushless motor.

10. The apparatus according to claim 3 wherein the hollow motor is a direct-current contactless or brushless motor.

11. The apparatus according to claim 5 wherein the hollow motor is a direct-current contactless or brushless motor.

12. The apparatus according to claim 1 wherein the hollow type motor provides for a shift of the at least one mobile element at an angle ranging from 320° to 350° about a given direction.

13. The apparatus according to claim 2 wherein the hollow type motor provides for a shift of the at least one mobile element at an angle ranging from 320° to 350° about a given direction.

14. The apparatus according to claim 3 wherein the hollow type motor provides for a shift of the at least one mobile element at an angle ranging from 320° to 350° about a given direction.

15. The apparatus according to claim 5 wherein the hollow type motor provides for a shift of the at least one mobile element at an angle ranging from 320° to 350° about a given direction.

16. The apparatus according to claim 8 wherein the hollow type motor provides for a shift of the at least one mobile element at an angle ranging from 320° to 350° about a given direction.

17. The apparatus according to claim 1 comprising a brake.

18. The apparatus according to claim 2 comprising a brake.

19. The apparatus according to claim 3 comprising a brake.

20. The apparatus according to claim 5 comprising a brake.

21. The apparatus according to claim 8 comprising a brake.

22. The apparatus according to claim 12 comprising a brake.

23. The apparatus according to claim 17 wherein the brake is a failsafe brake.

24. The apparatus according to claim 1 wherein the at least one hollow motor comprises:
   a first hollow motor;
   a second hollow motor;
   the first and second hollow motors being oriented orthogonal to each other.

25. The apparatus according to claim 2 wherein the at least one hollow motor comprises:
   a first hollow motor;
   a second hollow motor;

the first and second hollow motors being oriented orthogonal to each other.

26. The apparatus according to claim 3 wherein the at least one hollow motor comprises:
a first hollow motor;
a second hollow motor;
the first and second hollow motors being oriented orthogonal to each other.

27. The apparatus according to claim 5 wherein the at least one hollow motor comprises:
a first hollow motor;
a second hollow motor;
the first and second hollow motors being oriented orthogonal to each other.

28. The apparatus according to claim 8 wherein the at least one hollow motor comprises:
a first hollow motor;
a second hollow motor;
the first and second hollow motors being oriented orthogonal to each other.

29. The apparatus according to claim 12 wherein the at least one hollow motor comprises:
a first hollow motor;
a second hollow motor;
the first and second hollow motors being oriented orthogonal to each other.

30. The apparatus according to claim 17 wherein the at least one hollow motor comprises:
a first hollow motor;
a second hollow motor; the first and second hollow motors being oriented orthogonal to each other.

31. The apparatus according to claim 23 wherein the at least one hollow motor comprises:
a first hollow motor;
a second hollow motor;
the first and second hollow motors being oriented orthogonal to each other.

32. The apparatus according to claim 1 wherein
parts of the apparatus are connected by cables or wires; and
the cables or wires pass through the at least one hollow motor.

33. The apparatus according to claim 2 wherein
parts of the apparatus are connected by cables or wires; and
the cables or wires pass through the at least one hollow motor.

34. The apparatus according to claim 3 wherein
parts of the apparatus are connected by cables or wires; and
the cables or wires pass through the at least one hollow motor.

35. The apparatus according to claim 5 wherein
parts of the apparatus are connected by cables or wires; and
the cables or wires pass through the at least one hollow motor.

36. The apparatus according to claim 8 wherein
parts of the apparatus are connected by cables or wires; and
the cables or wires pass through the at least one hollow motor.

37. The apparatus according to claim 12 wherein
parts of the apparatus are connected by cables or wires; and
the cables or wires pass through the at least one hollow motor.

38. The apparatus according to claim 17 wherein
parts of the apparatus are connected by cables or wires; and
the cables or wires pass through the at least one hollow motor.

39. The apparatus according to claim 23 wherein
parts of the apparatus are connected by cables or wires; and
the cables or wires pass through the at least one hollow motor.

40. The apparatus according to claim 24 wherein
parts of the apparatus are connected by cables or wires; and
the cables or wires pass through the at least one hollow motor.

41. The apparatus according to claim 1 wherein the at least one hollow motor and the at least one mobile element provides a direct transmission for rotation and a gear reduction ratio of 1.

42. The apparatus according to claim 2 wherein the at least one hollow motor and the at least one mobile element provides a direct transmission for rotation and a gear reduction ratio of 1.

43. The apparatus according to claim 3 wherein the at least one hollow motor and the at least one mobile element provides a direct transmission for rotation and a gear reduction ratio of 1.

44. The apparatus according to claim 5 wherein the at least one hollow motor and the at least one mobile element provides a direct transmission for rotation and a gear reduction ratio of 1.

45. The apparatus according to claim 8 wherein the at least one hollow motor and the at least one mobile element provides a direct transmission for rotation and a gear reduction ratio of 1.

46. The apparatus according to claim 12 wherein the at least one hollow motor and the at least one mobile element provides a direct transmission for rotation and a gear reduction ratio of 1.

47. The apparatus according to claim 17 wherein the at least one hollow motor and the at least one mobile element provides a direct transmission for rotation and a gear reduction ratio of 1.

48. The apparatus according to claim 23 wherein the at least one hollow motor and the at least one mobile element provides a direct transmission for rotation and a gear reduction ratio of 1.

49. The apparatus according to claim 24 wherein the at least one hollow motor and the at least one mobile element provides a direct transmission for rotation and a gear reduction ratio of 1.

50. The apparatus according to claim 32 wherein the at least one hollow motor and the at least one mobile element provides a direct transmission for rotation and a gear reduction ratio of 1.

51. The apparatus according to claim 1 wherein the hollow portion of the motor is oriented on the axis of the rotor and stator, and on the rotational axis about which the mobile elements may go into rotation.

52. The apparatus according to claim 51 wherein:
parts of the apparatus are connected by cables or wires; and
the cables or wires pass through the hollow portion of the hollow motor.

* * * * *